(12) United States Patent
Stone, III et al.

(10) Patent No.: US 7,675,294 B2
(45) Date of Patent: Mar. 9, 2010

(54) SYSTEM AND METHOD FOR DETERMINING ATTENUATION OF ELECTROMAGNETIC WAVES IMPACTING AN ELECTROMAGNETIC SHIELD

(75) Inventors: George F. Stone, III, Worcester, PA (US); Gilbert P. Condon, Audubon, PA (US)

(73) Assignee: TriTech Applied Sciences, Inc., Lansdale, PA (US)

( * ) Notice: Subject to any disclaimer, the term of this patent is extended or adjusted under 35 U.S.C. 154(b) by 297 days.

(21) Appl. No.: 11/715,540

(22) Filed: Mar. 8, 2007

(65) Prior Publication Data
US 2007/0241761 A1 Oct. 18, 2007

Related U.S. Application Data

(60) Provisional application No. 60/780,441, filed on Mar. 8, 2006.

(51) Int. Cl.
*G01R 29/00* (2006.01)
(52) U.S. Cl. .................................. 324/627
(58) Field of Classification Search ............ 324/627
See application file for complete search history.

(56) References Cited

U.S. PATENT DOCUMENTS

| | | | |
|---|---|---|---|
| 3,492,568 A | 1/1970 | Johnson |
| 4,831,210 A | 5/1989 | Larson |
| 4,962,358 A | 10/1990 | Svetanoff |
| 5,068,616 A | 11/1991 | Broyde |
| 5,153,524 A | 10/1992 | McCormack |
| 5,256,960 A | 10/1993 | Novini |
| 5,285,164 A | 2/1994 | Wong |
| 5,341,423 A * | 8/1994 | Nossen ................ 380/252 |
| 5,565,656 A | 10/1996 | Mottahed |
| 5,828,220 A | 10/1998 | Carney |
| 5,990,689 A | 11/1999 | Poncon |
| 6,144,341 A | 11/2000 | Kraz |
| 6,255,830 B1 | 7/2001 | Rollin |
| 6,525,657 B1 | 2/2003 | Wojcik |
| 6,526,365 B1 | 2/2003 | Marino |
| 6,987,392 B1 | 1/2006 | Hernandez |
| 2002/0058490 A1 | 5/2002 | Sorrells |
| 2004/0183529 A1 | 9/2004 | Kajiwara |
| 2005/0053008 A1 | 3/2005 | Griesing |

OTHER PUBLICATIONS

Klinkenbusch, Ludger, "*On the shielding effectiveness of enclosures*", IEEE Transactions on Electromagnetic Compatibility v 47 n 3 Aug. 2005, p. 589-601.

Ogunsola, A., "*Harmonization of shielding-effectiveness standards for enclosures*", Compliance Engineering v 18 n 3 2001; p. 52-60, 2001 (web-site format).

(Continued)

*Primary Examiner*—Vincent Q Nguyen
(74) *Attorney, Agent, or Firm*—RatnerPrestia

(57) ABSTRACT

A method for determining attenuation of electromagnetic waves impacting an electromagnetic shield. A reference amplitude is provided. A signal exhibiting a first frequency is converted to a converted signal exhibiting a second frequency higher than the first frequency. Electromagnetic waves corresponding to the converted signal are transmitted from a first antenna toward a second antenna with the electromagnetic shield positioned between them. Attenuated remnants of the electromagnetic waves received by the second antenna are converted to a corresponding signal exhibiting a third frequency that is lower than the second frequency. The amplitude of the corresponding signal is compared to the reference amplitude.

17 Claims, 6 Drawing Sheets

OTHER PUBLICATIONS

Hooks, B.L.; Aughinbaugh, D.W., *"Electromagnetic Shielding Measurements—NMR (Nuclear Magnetic Resonance) Enclosure"*, AMSMI/RT-85-6-TR; SBI-AD-E950 743, Dec. 21, 1984.

Nielsen, P.H., *"Radio Frequency Shielding Tests of System Technology Test Facility at Meck Island, Marshall Islands"*, CERL-SR-E-107 Jun. 1977.

Hobbins, K.A.W., *"Ensuring the shielding of cabinets and enclosures"*, New Electronics, vol. 20, No. 14 1987 (Abstract Only).

United States Government, Department of Defense, "Military Standard Attenuation Measurements for Enclosures, Electromagnetic Shielding, for Electronic Test Purposes, Method of", MIL-STD-285, Jun. 25, 1956.

* cited by examiner

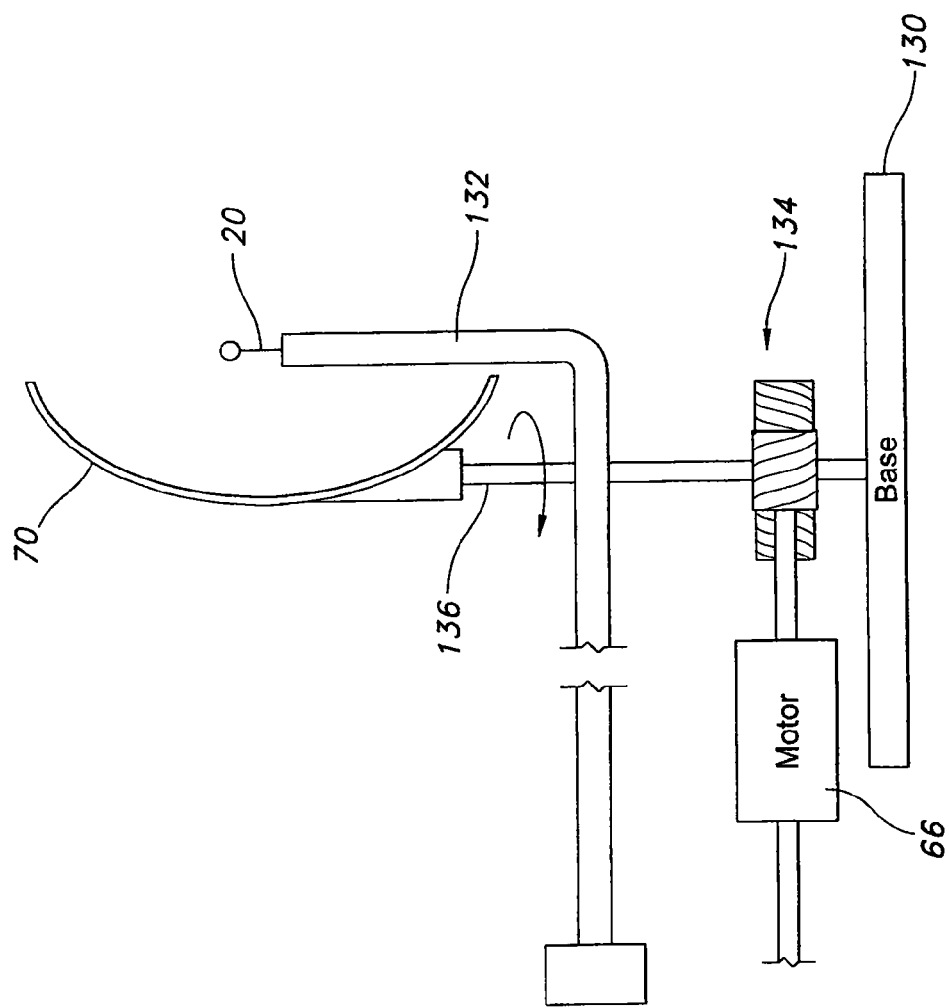

SYSTEM AND METHOD FOR DETERMINING ATTENUATION OF ELECTROMAGNETIC WAVES IMPACTING AN ELECTROMAGNETIC SHIELD

RELATED APPLICATION

This application claims the benefit of priority to U.S. Provisional Application Ser. No. 60/780,441, filed Mar. 8, 2006, the contents of which are incorporated by reference herein.

BACKGROUND OF THE INVENTION

The field of this invention is a system and method for determining the attenuation of electromagnetic waves by an electromagnetic shield, which may include any material or path designed to cause, or resulting in, any partial or complete loss of electromagnetic signal strength.

Shielded enclosures or shelters are utilized in various industries to shield electromagnetic waves from propagating through the shield of a shelter or enclosure. For example, an electromagnetic shield can be used for security purposes where it is necessary to prevent electromagnetic emanations from leaving the enclosure or shelter or to prevent electromagnetic emanations from entering the enclosure or shelter. In the case of a shielded building, for example, it may be important to shield every wall in the building. Shielded enclosures may also be used with medical diagnostic equipment such as MRI (magnetic resonance imaging) equipment where it may be important to prevent outside electromagnetic emanations from affecting the equipment's ability to perform accurately. They may also be used for rooms that are used to test electronic equipment where it is important to prevent electromagnetic emanations either from entering the room or from leaving the room.

It is often important to test the ability of the shielded enclosure to perform its shielding function. The effectiveness of the shielded enclosure is measured by introducing electromagnetic waves of known amplitude and frequency on one side of the shielded enclosure and receiving the electromagnetic waves on the other side of the shielded enclosure. The difference or other relationship between the two amplitudes is a measure of the attenuation of the shield. Some methods and equipment that may be used to perform such a test is disclosed in MIL-STD-285, Jun. 25, 1956, in NSA 65-6, and in NSA 65-5. The higher the attenuation the greater the effectiveness of the shield. Thus, attenuation is a measure of shielding effectiveness.

Various shielding materials and techniques perform differently depending on the type of electromagnetic field and the frequency of the waves being generated. Because each frequency range has its own particular characteristics, an electromagnetic shield will react differently to different waves exhibiting different frequencies. Exemplary materials can include exotic metals, other metals, air, fluids and other shielding materials.

In order to perform electromagnetic testing on shielded shelters or enclosures, two subsystems are used, one subsystem to generate the waves on one side of the shield or enclosure and another subsystem on the other side of the shield or enclosure to receive the waves. The waves used for testing may be generated in various frequency ranges. One such range used for testing is a microwave frequency range that may vary from about 10 GHz to about 10.3 GHz. A difficulty with using a frequency in this range is that corresponding signals do not propagate through wire without a high level of loss. Standard coaxial cable (such as RG58 or other lower cost cable) has a high level of loss through the cable. Utilizing low loss cable improves the problem of high loss but does not eliminate it and poses additional problems. Low loss cable is not practical due to its fragile construction and stiffness and is damaged very easily. In both cases (low cost and low loss cable) the cable lengths must be kept short to minimize loss of signal amplitude which results in decreased testing capability in the form of loss of dynamic range. Dynamic range is defined as the highest level to the lowest level of signal amplitude that can be measured.

The generation side of the system can sometimes be kept close to the transmitting antenna thereby minimizing the loss of signal amplitude between a source of waves and an antenna that transmits the waves. But on the receiving side of the system, the receiving antenna must be moved to various positions about the shelter or enclosure and preferably not be kept close to an analyzer without significant difficulty. Moving the receiving antenna can be done; but this necessitates moving the receiver electronics along with the receiving antenna which is cumbersome and takes time during the testing.

SUMMARY OF THE INVENTION

An exemplary embodiment of the present invention is a system for determining a level of amplitude attenuation of electromagnetic waves impacting an electromagnetic shield. The exemplary embodiment has a first converter receiving a first signal exhibiting a first frequency and converting the first signal to a second signal exhibiting a second frequency higher than the first frequency. A first antenna is positioned on a side of the electromagnetic shield receiving the second signal for transmitting corresponding electromagnetic waves substantially exhibiting the second frequency toward a second antenna positioned on another side of the electromagnetic shield. The second antenna receives attenuated remnants of the electromagnetic waves attenuated by the electromagnetic shield and provides a corresponding third signal substantially exhibiting the third frequency. A second frequency converter converts the third signal to a fourth signal exhibiting a third frequency that is lower than the second frequency for transmission to a measuring receiver.

Another exemplary embodiment of the present invention is a method for determining an attenuation level of electromagnetic waves impacting an electromagnetic shield. A reference amplitude is provided. A signal exhibiting a first frequency is converted to a converted signal exhibiting a second frequency higher than the first frequency. Electromagnetic waves corresponding to the converted signal are transmitted from a first antenna toward a second antenna with the electromagnetic shield positioned between the first and second antennas. Attenuated remnants of the electromagnetic waves received by the second antenna are converted to a corresponding signal exhibiting a third frequency that is lower than the second frequency. The amplitude of the corresponding signal is determined. The amplitude of the corresponding signal is compared to the reference amplitude.

BRIEF DESCRIPTION OF THE DRAWINGS

FIG. 5 is a more detailed illustration of an antenna system that includes an omnidirectional antenna and a rotating reflector.

DETAILED DESCRIPTION OF THE INVENTION

The inventors make use of the propagation of signals or waves in lower frequency VHF ranges (100 MHz in an exemplary embodiment) because such waves or signals can propagate through inexpensive and easy to use coaxial cables with minimal power loss. Exemplary embodiments of the invention utilize this phenomenon to mitigate the problems identified above.

Exemplary embodiments of the invention have been designed to utilize the low frequency characteristics of lower frequency signals or waves to perform high frequency testing. Exemplary embodiments of the invention use frequency division and frequency multiplication. Frequency division is also known as frequency down-conversion. Frequency multiplication is also known as frequency up-conversion.

Figure 1:
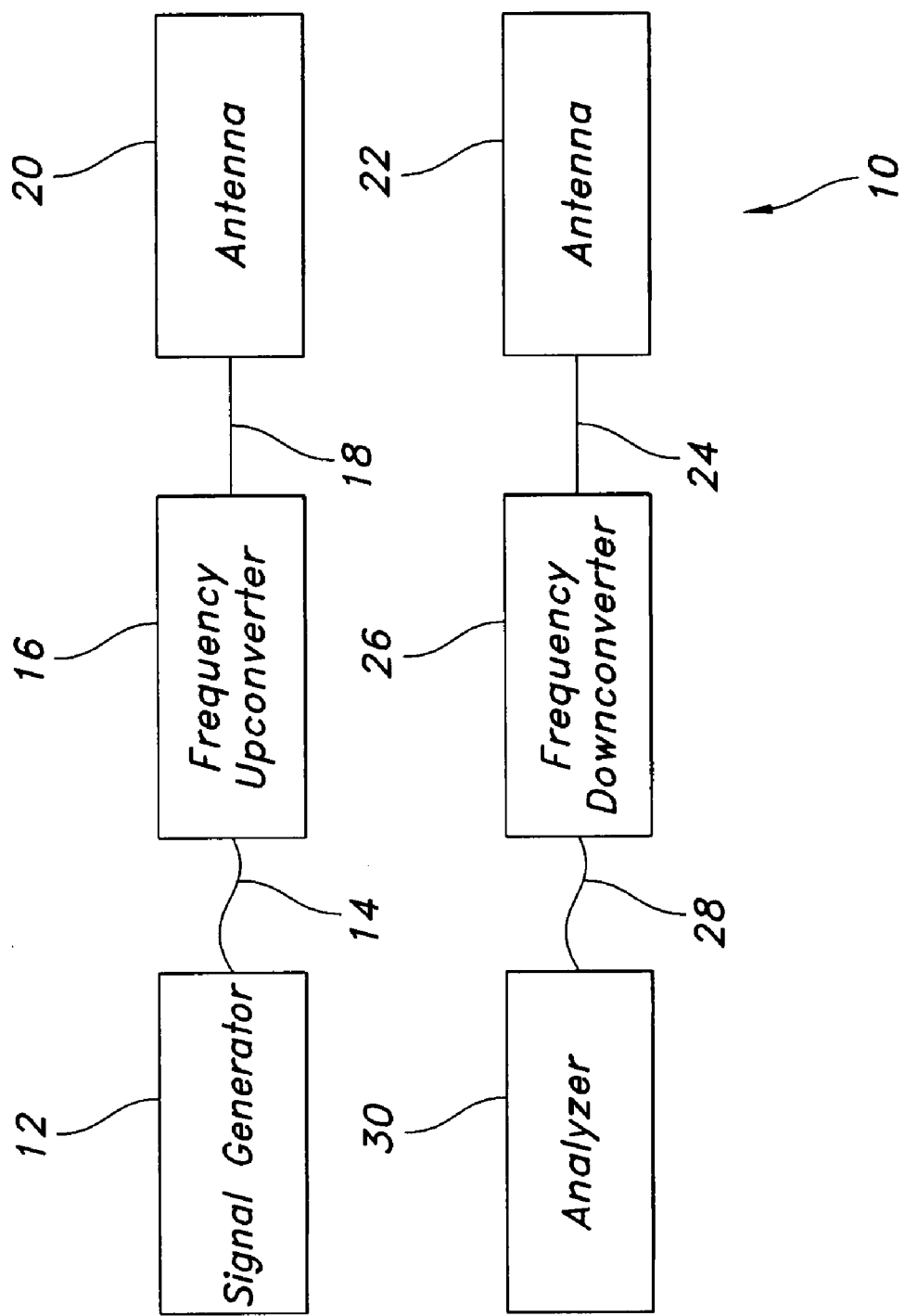
FIG. 1 is a block diagram illustrating a system in accordance with an exemplary embodiment of the present invention.

FIG. 1 is a block diagram illustrating a system 10 in accordance with an exemplary embodiment of the present invention. The system illustrated in FIG. 1 is or may be used in two stages. In a first stage, the system is used without an electromagnetic shield being positioned between a first antenna and a second antenna and a reference amplitude of a signal is determined. In a second stage, the system is used with an electromagnetic shield being positioned between the first and second antennas and a second amplitude of a signal is determined. In the second stage, for example, the first antenna may be positioned inside an electromagnetically shielded shelter or enclosure such as a room and the second antenna may be positioned outside the electromagnetically shielded shelter or enclosure. The second amplitude may then be compared to the reference amplitude. The resulting comparison may be an indication of the attenuation capability of the electromagnetic shield. It will be understood by those of ordinary skill in the art that the stages may be performed in any order. That is, the reference amplitude can be determined first, without the electromagnetic shield being positioned between the two antennas. Alternatively, an amplitude measurement may first be obtained with the electromagnetic shield placed between the two antennas and then an amplitude can be determined without the electromagnetic shield being positioned between the two antennas in order to determine a reference amplitude.

We will first describe how an exemplary embodiment of the invention is used with an electromagnetic shield being placed between the two antennas. Referring to FIG. 1, a signal generator 12 may produce a first signal, which may exhibit a low first frequency. The first signal may be generated with a known amplitude. In an exemplary embodiment, the frequency of the signal generated by signal generator 12 may be selected from a range of low VHF megahertz signals ranging from about 163 MHz to about 10 GHz. In an alternative embodiment, signal generator 12 may produce a signal exhibiting a frequency either below 163 MHz or above 10 GHz. A low megahertz signal or other low frequency signal may be selected because equipment to generate such a low frequency signal is relatively inexpensive to purchase and because low frequency signals may be propagated through cable without a high level of loss. In an alternative embodiment, signal generator 12 may generate a signal exhibiting between about 900 MHz and about 1 GHz. In other alternative embodiments, signal generator 12 may generate a signal exhibiting other frequencies that may be considered to be low in the context of the shielded shelter or enclosure being tested and in the context of the connection cabling being used.

The low frequency signal produced by signal generator 12 may be propagated through a cable 14 to a first frequency converter 16 which may also be referred to as a frequency multiplier or frequency up-converter. Cable 14 may be coaxial cable or a similarly acting cable. In an exemplary embodiment, cable 14 may, if necessary be longer than a cable transmitting a signal exhibiting a higher frequency because low frequency signals propagate with less loss than high frequency signals.

Up-converter 16 may change the first signal to a second signal exhibiting a second frequency that is higher than the first frequency. In an exemplary embodiment, the second frequency may be selected from a range of gigahertz frequencies ranging from about 9 GHz to about 12 GHz and, in one exemplary embodiment, is optionally about 10 GHz. Frequencies produced by frequency up-converter 16 may be in a microwave GHz range when it is necessary to test an electromagnetic shield or enclosure designed to shield electromagnetic emanations in a microwave GHz frequency range. In alternative embodiments, frequency up-converter 16 may provide a frequency in another range which may be needed to test an electromagnetic shield or enclosure intended to shield a frequency in such other range.

The second signal exhibiting the second higher frequency may be transmitted to a first antenna 20 over a cable 18. In an exemplary embodiment, a length of cable 18 may be relatively short to enable frequency up-converter 16 to be placed at or very near antenna 20. In an exemplary embodiment, antenna 20 should be as close as possible to frequency up-converter 16 in order to minimize loss of amplitude of the high frequency signal between up-converter 16 and antenna 20. In an exemplary embodiment, the length of cable 18 may be in a range from about three inches to about six feet, depending upon the dynamic range, but may be longer or shorter in alternative embodiments. In an alternative embodiment, a waveguide tube may be used instead of cable 18 in order to further reduce the amount of power loss. In an exemplary embodiment, antenna 20 may be an omnidirectional antenna. When antenna 20 is an omni-directional antenna, it may be used in conjunction with a rotating reflector 70 which may sweep a center lobe of the electromagnetic waves emanating from antenna 20 about the inside of the walls of a shielded shelter or enclosure. A more detailed description of an exemplary antenna system that includes omni-directional antenna 20 and reflector 70 are shown in connection with FIGS. 3 and 5, discussed below.

Antenna 20 may convert the second signal to electromagnetic waves substantially exhibiting the second frequency and may transmit the electromagnetic waves toward an electromagnetic shield (not shown) that may be part of an electromagnetically shielded shelter or enclosure. More specifically, antenna 20 may be on one side of the electromagnetic shield or enclosure. Even more specifically, it may be inside an electromagnetically shielded shelter or enclosure, but is alternatively positioned outside an electromagnetically shielded shelter or enclosure. Electromagnetic waves from antenna 20 may impact or illuminate the electromagnetic shield.

Although portions of the electromagnetic waves may not pass through the electromagnetic shield, other portions of the electromagnetic waves may pass through the shield. The portions of the electromagnetic waves that pass through the shield are attenuated remnants of the electromagnetic waves and may be received by a second antenna 22. In an exemplary embodiment, second antenna 22 may be a high gain, directional horn antenna that may operate in a range from about 8.2 GHz to about 12.4 GHz at about −20 dB. For example, second antenna 22 may be a high gain, directional horn antenna providing a gain in a range of about 12 to about 15 dB. In an alternative embodiment, antenna 22 may operate in a different frequency range where the lower end of the range may be lower than 8.2 GHz and the higher end of the range may be higher than 12.4 GHz and at a greater or lesser gain.

Second antenna 22 may be positioned on a second side of the electromagnetic shield, shelter, or enclosure. In the case of a shielded shelter or enclosure, for example, antenna 22 may be outside the shelter or enclosure. The remnants of the electromagnetic waves received by second antenna 22 may be converted to a third signal. The frequency of the third signal may be substantially the same frequency as the electromagnetic waves transmitted by antenna 20 and received by antenna 22. The third signal may be propagated over cable 24 to a second frequency converter 26, which may also be referred to as a frequency divider or frequency down-converter 26. In an exemplary embodiment, cable 24 may be very short to enable frequency down-converter 26 to be placed at or very near antenna 22. In an exemplary embodiment, antenna 22 should be as close as possible to frequency down-converter 26 in order to minimize loss of power of the signal between frequency down-converter 26 and antenna 20. In an exemplary embodiment, the length of cable 24 may be about four inches, but may be longer or shorter in alternative embodiments. In an alternative embodiment, a waveguide tube may be used instead of cable 24 in order to further reduce the amount of power loss.

Second frequency down-converter 26 may change the third signal to a fourth signal exhibiting a third frequency. The third frequency may be lower than the second frequency. In an exemplary embodiment, the third frequency may be selected from a VHF range of megahertz frequencies ranging from about 100 MHz to about 250 MHz, although lower and higher frequencies are optionally selected. In alternative embodiments, other frequencies may be provided by frequency down-converter 26 in other ranges which allow a system to use a low cost frequency down-converter and a low cost analyzer 30. The amplitude of the third signal may be substantially proportional to the amplitude of the remnants of the electromagnetic waves received by antenna 22.

After frequency down-converter 26 converts the third signal to a fourth signal exhibiting a low third frequency, the fourth signal may be transmitted at substantially the low frequency through less expensive and easy to use cable 28 to an analyzer 30. Analyzer 30 may be a measuring receiver that may measure the amplitude of the fourth signal. Afterward, a comparison may be made between the amplitude of a reference signal with the amplitude of the of the fourth signal. This comparison may provide an indication of the attenuation capability by the shielded shelter or enclosure.

In order to determine the amplitude of a reference signal, the system described above and illustrated in FIG. 1 may be used without an electromagnetic shield positioned between antennas 20 and 22. When the system illustrated in FIG. 1 is operated without such an electromagnetic shield, the higher amplitude of the signal received by measuring receiver 30 may be used as a reference signal.

It will be understood by those skilled in the art, that in an alternative embodiment, a reference amplitude may be produced by another system or by another method. Regardless of how the reference amplitude is produced, the reference amplitude may be compared with the amplitude received by measuring receiver 30 when an electromagnetic shield has been positioned between antennas 20 and 22.

An advantage of an exemplary embodiment of this invention is that it allows an electromagnetic shield to be more easily tested using high frequency waves than with a conventional system. Another advantage is that the antennas can be placed in more meaningful locations because receiving antenna 22 may be moved independently of the analyzer because the low frequency of the fourth signal allows cable 28 to be longer than was possible using a prior art system. That is, receiving antenna 22 may be more easily moved relative to a shielded shelter or enclosure to perform a sweep test such as a physical sweep test. Sweeping over some or all surfaces may provide a more comprehensive test when testing an enclosure than fixed point testing. Although the prior art apparatus allows relatively small amounts of sweeping in limited increments, such incremental sweeping is difficult and cumbersome to do. In an exemplary embodiment, cable 28 may be about 100 feet to 150 feet long, or longer.

Figure 2:
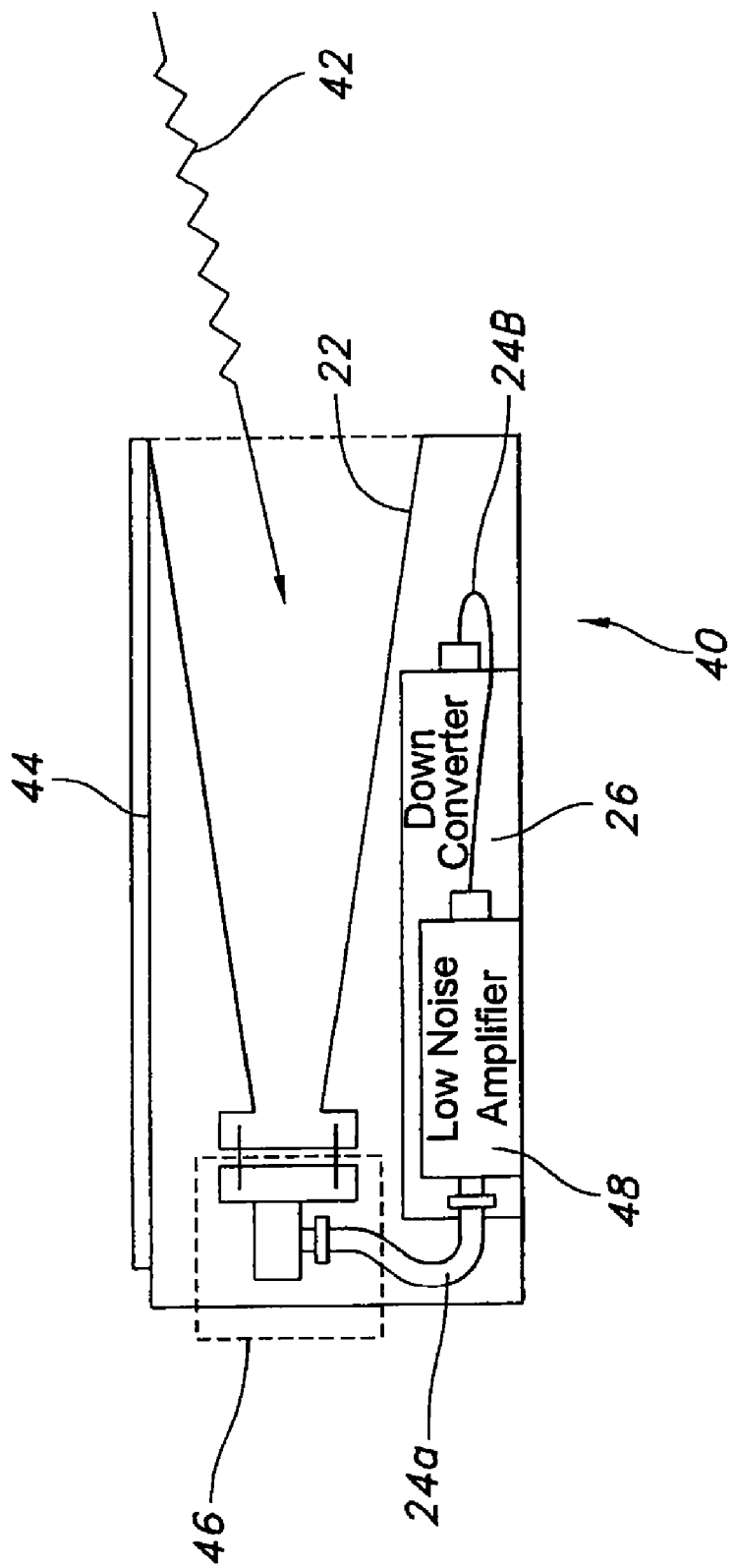
FIG. 2 is a block diagram of an exemplary stand-alone receiver that may be a subsystem of the system illustrated in FIG. 1.

Referring to FIG. 2, a block diagram of an exemplary receiver 40 is shown that may comprise a portion of the system illustrated in FIG. 1. FIG. 2 shows a carrying case 44 that may be small enough to be hand-held containing receiving antenna 22 and related elements on the receiving side of the system. FIG. 2 illustrates electromagnetic waves 42 being received by antenna 22. Electromagnetic waves 42 may have been propagated by antenna 20 or by another antenna. In an exemplary embodiment, electromagnetic waves may be in a microwave range, for example, between about 10.0 GHz and 10.3 GHz. As illustrated in FIG. 2, after electromagnetic waves 42 are received by antenna 22, waveguide to SMA adapter 46 may then convert the waves 42 into a signal substantially exhibiting the same frequency as waves 42. The signal may then be propagated over cable 24A to a low noise amplifier 48 which may amplify the signal to maximize the dynamic range. The electrical signal from amplifier 48 may then be propagated over cable 24B to frequency down-converter 26. Frequency down-converter 26 may convert the signal to a converted signal exhibiting a converted frequency that is lower than the frequency of received waves 42 and the frequency of the signal from antenna 22. In an exemplary embodiment, the frequency of the converted signal may be in a VHF range, for example 163 MHz+/− about 50 MHz. The converted signal may then be propagated from down-converter 26 in receiver 40 to a measuring receiver such as analyzer 30 in FIG. 1.

Hand-held receiver 40, optionally housed in carrying case or chassis 44, may allow antenna 22 to be more easily swept along an outside of a shelter or enclosure because it is a lightweight unit that converts microwave high frequency waves 42 to a low frequency signal and allows the use of relatively longer cabling between hand-held receiver 40 and measuring receiver 30.

Figure 3:
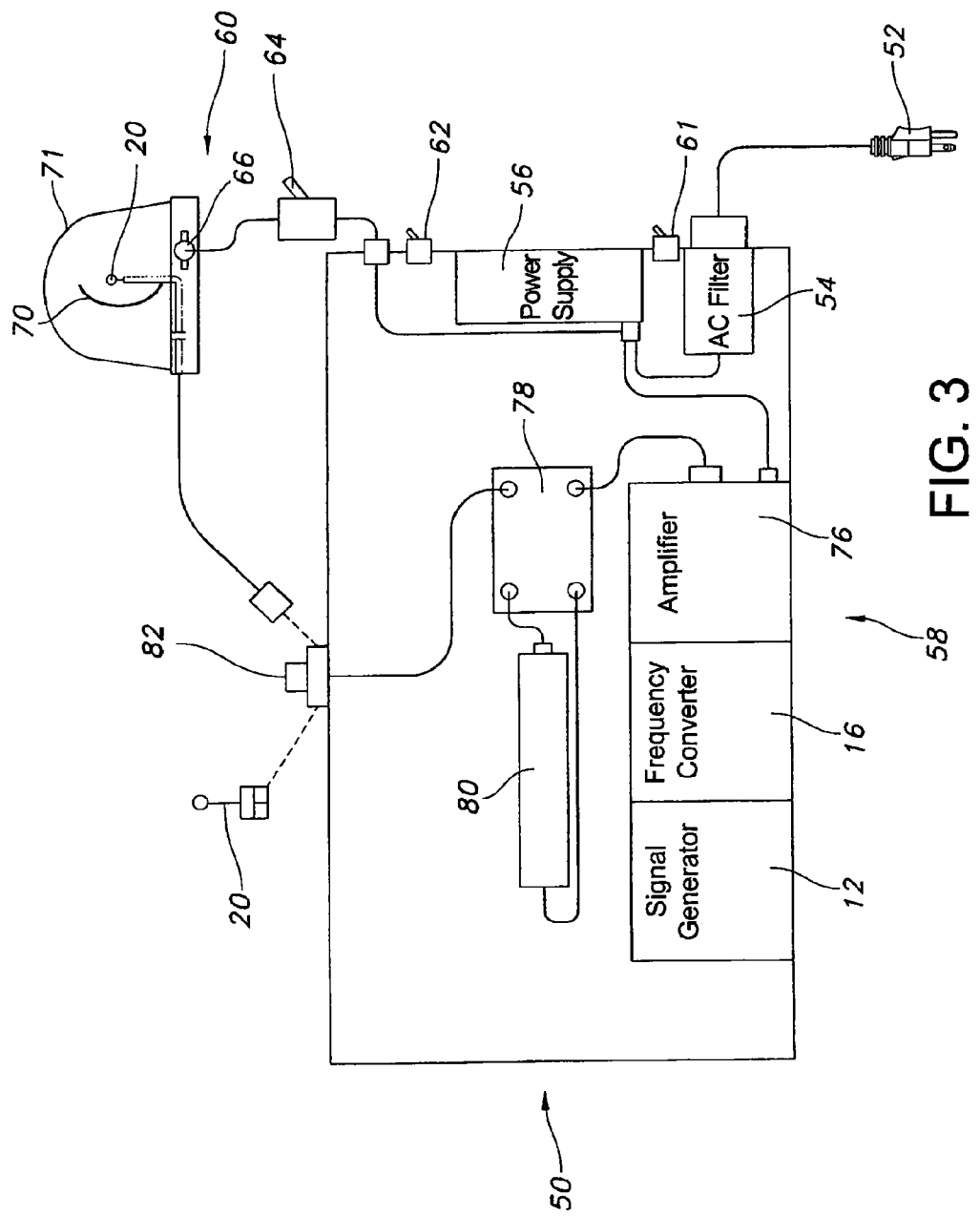
FIG. 3 is a block diagram of an exemplary stand-alone transmitter that may be a subsystem of the system illustrated in FIG. 1.

Referring to FIG. 3, a block diagram of an exemplary stand-alone transmitter 50 is shown that may constitute a portion of the system illustrated in FIG. 1. In FIG. 3, a power plug 52 may supply power to stand-alone transmitter 50 from which power may be provided to section 58 and to section 60. Current may first pass through an on-off power switch 61 and an AC filter 54 which may filter the power and may provide power to an AC/DC power supply 56, supplying power to motor 66, which may be a DC motor, through calibration switch 62 and on-off switch 64. In turn, motor 66 may rotate a reflector 70 about omnidirectional antenna 20 to sweep a focused center lobe of electromagnetic waves about the inside of a shielded shelter or enclosure. In an alternative embodiment, antenna 20 may be a directional antenna.

FIG. 5 is a more detailed illustration of an antenna system that includes omnidirectional antenna 20 and a rotating reflector 70. Referring to FIG. 5, antenna 20 may be positioned at a focal point of rotating reflector 70. A length of the omnidirectional antenna may be one-quarter of a wavelength of the electromagnetic waves being transmitted by antenna 20. Reflector 70 may be a made from a metalized plastic or other material that is able to focus electromagnetic waves emanating from omnidirectional antenna 20 in a desired direction. Using a reflector to sweep the electromagnetic waves may result in waves exhibiting a substantial gain over in signal strength being directed toward the inside of the shielded shelter or enclosure relative to the signal strength without the reflector. Referring to FIG. 3, the antenna 20 and rotating reflector 70 may be covered with a cover 71 which may be made of plastic or other material which may be transparent to the electromagnetic waves emanating from antenna 20 and which may protect the antenna 20 and reflector 70 from physical damage.

Reflector 70 is operable to reflect electromagnetic waves from the omnidirectional antenna toward the inside of the shielded shelter or enclosure so as to sweep a focused center lobe of the electromagnetic waves emanating from antenna 20 in a plurality of directions. In an exemplary embodiment, the electromagnetic waves may be swept along a 360° arc inside the shielded shelter or enclosure. By sweeping a center lobe in a 360° arc, the reflector may be able to sweep the electromagnetic waves about all or a significant portion of the inside walls of the shielded shelter or enclosure. Alternatively, the reflector may sweep the electromagnetic waves in an arc that is less than 360° if it is appropriate to do so. For example, the reflector may sweep the electromagnetic waves along only one side of the shielded shelter or enclosure; or it may sweep the waves along more than one side. In addition, the rotating antenna may be able to sweep a ceiling and/or a floor of the shelter or enclosure.

The antenna system illustrated in FIG. 5 may be mounted onto a base assembly 130. An RF signal may be transmitted to antenna 20 over a shielded cable 132. Shielded cable 132 may also function to maintain antenna 20 at the focal point of rotating reflector 70. Reflector 70 may be coupled to motor 66 through a gear adapter mechanism 134 and a rotating spindle 136. Motor 66 and gear adapter mechanism 134 may be able to rotate spindle in a 360° arc. As spindle 136 rotates, it may also rotate reflector 70 about antenna 20.

AC/DC power supply 56 may also supply power to section 58 comprising a frequency source oscillator 12 which may be the signal generator 12 illustrated in FIG. 1, frequency up-converter 16, and RF output amplifier 76. In an exemplary embodiment, RF output amplifier 76 may be a 10 GHz amplifier providing 1.5 watts of power. In an alternative embodiment, amplifier 76 may operate at a different frequency, for example, another frequency in a microwave range, or in a frequency range higher than a microwave frequency range, and may provide a higher or lower amount of power depending upon the dynamic range needed for the testing. Dynamic range is the amount of measurable source less the quietest level of noise measurable in the absence of the source signal. Dynamic range may define the maximum level of shielding measurable with the system. In acoustic terms, it may be the loudest noise minus the quietest noise that may be measurable.

Power from amplifier 76 may be transmitted through a relay 78 and then to an SMA RF output terminal 82 for powering antenna 20. Relay 78 may also be connected to an attenuator 80 which may attenuate the power produced by amplifier 76 to antenna 20. In an exemplary embodiment, attenuator 80 may be a 60 dB attenuator. In an alternative embodiment, attenuator 80 may have a different attenuation capability depending upon the dynamic range required for the test. Using such an attenuator may allow the use of a lower power wave from antenna 20, thereby providing a more sensitive reading at analyzer 30. Attenuator 80 may prevent a large signal from saturating analyzer 30. Attenuator 80 may also be used to test the ability of the measuring receiver to make an accurate attenuation determination.

In an exemplary embodiment, amplitudes of signals may be received by analyzer 30 under two operative modes. In the first mode, a signal received by analyzer 30 has not been attenuated by attenuator 80. In the second mode, another signal received by analyzer 30 by has been attenuated by attenuator. If analyzer 30 is operating accurately, the amplitude of the other signal received by analyzer 30 should be reduced by a value that is equal to the amount of attenuation caused by attenuator 80.

When relay 78 is in a first condition, current from amplifier 76 may be transmitted directly to output terminal 82, bypassing attenuator 80. When relay 78 is in a second condition, current from amplifier 76 may be transmitted to output terminal 82 through attenuator 80.

The exemplary embodiments of the devices described herein may be used with pre-existing testing systems as add-ons. The exemplary add-ons may provide additional testing capability to pre-existing testing systems with minimal additional investment. The exemplary embodiments may be used independently on either the up-convert side or on the down-convert side, or both. The up-converter side (elements 12 to 20 in FIG. 1 and the stand-alone unit illustrated in FIG. 3) may be used to generate high frequency waves from a low frequency source for determining the attenuation capability of a shielded enclosure or shelter. The up-converter side may be used to generate such electromagnetic waves from wall power. An advantage is that low frequency wave generation is less expensive and more readily available than a generator of high frequency waves. High frequency wave generation would otherwise require procurement of a high frequency generator and amplifier in addition to a low frequency generator. The exemplary embodiments described above eliminate the need for the high frequency generator and amplifier. The up-converter side may be used with standard microwave receivers. Alternatively the up-converter side may be used with the hand-held down-converter side.

The exemplary down-converter side may also be used with a standard microwave generator. The advantage of this approach is to provide better mobility for the receiver antenna and the use of less expensive cabling.

Figure 4A:
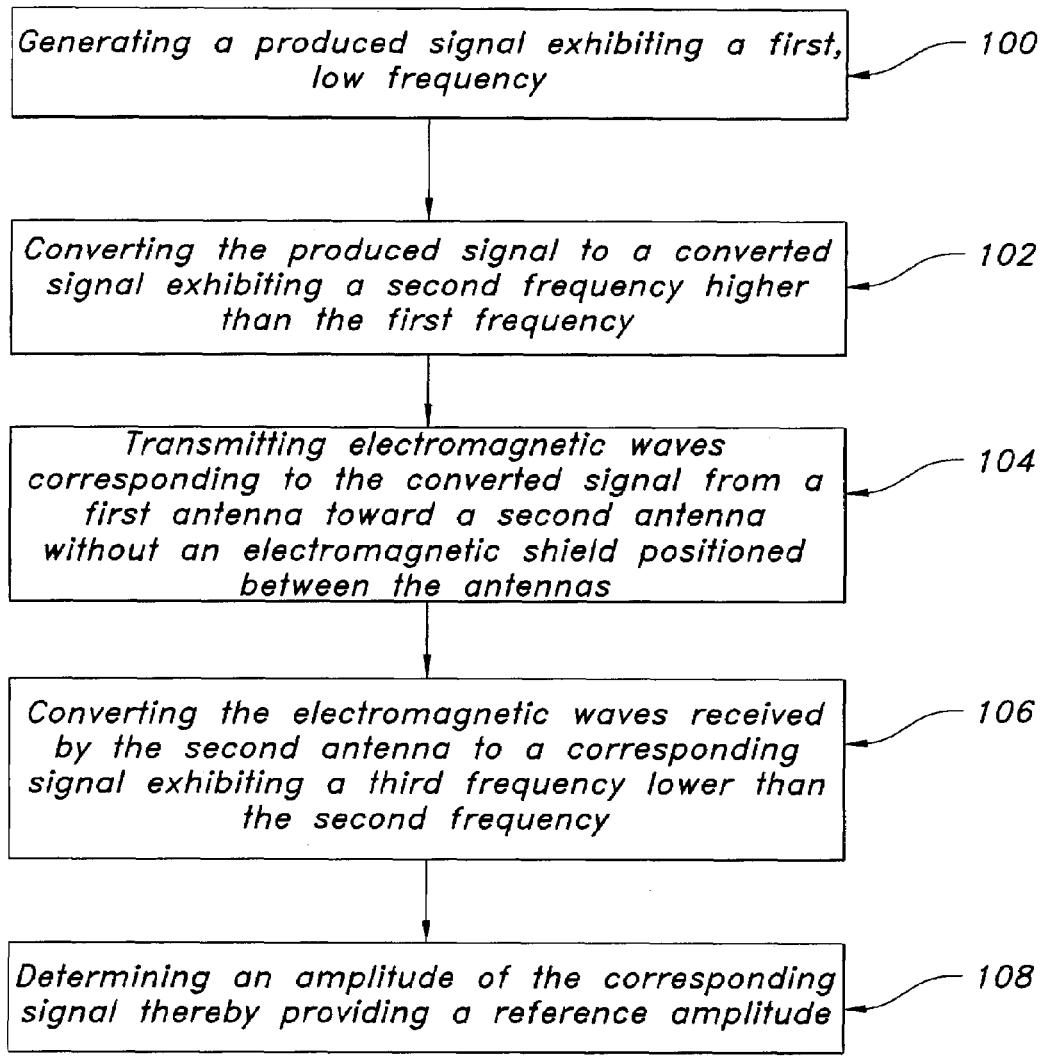
FIG. 4A is a block diagram of a method that may be used to determine an attenuation level of an electromagnetic shield.
Figure 4B:
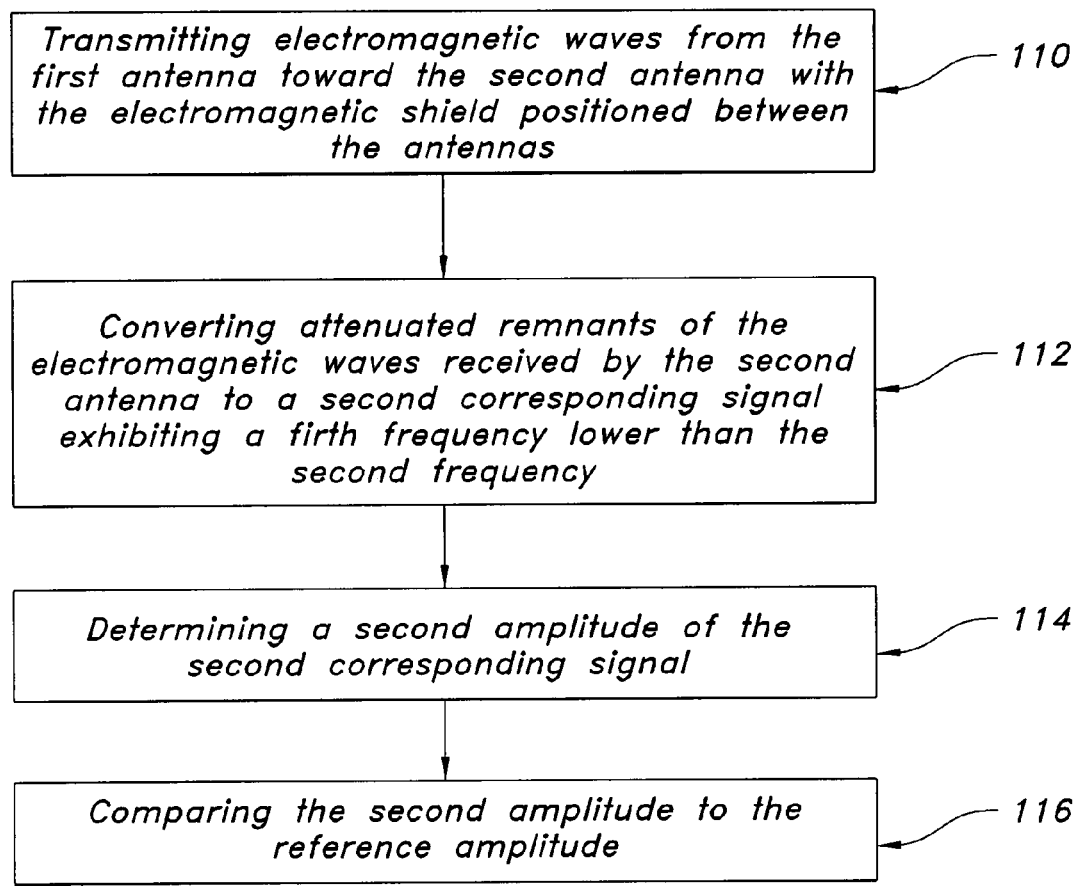
FIG. 4B is a block diagram of a method that may be used to determine an attenuation level of an electromagnetic shield.

An exemplary method that may be followed will now be described in conjunction with the block diagrams shown in FIGS. 4A and 4B. FIG. 4A is a block diagram of a method that may be used when an electromagnetic shield is not positioned between two antennas in accordance with an exemplary embodiment of the present invention (e.g., for calibration purposes). FIG. 4B is a block diagram of a method that may be used when an electromagnetic shield is positioned between two antennas in accordance with exemplary embodiment of the present invention.

Referring to FIG. 4A, in Step 100, a first produced signal is generated that exhibits a first, low frequency in a VHF radiofrequency range. In an exemplary embodiment, the frequency of the signal generated in Step 100 may be in a range from about 163 MHz to about 1 GHz. Other frequencies may be generated in other embodiments. In Step 102, the produced signal generated in Step 100 is converted to a converted signal exhibiting a frequency that is higher than the first frequency.

In an exemplary embodiment, the frequency of the converted signal in Step 102 may be in a range from about 10.0 GHz to about 10.3 GHz. In other embodiments, the frequency of the converted signal may be selected from a different range of frequencies depending upon the characteristics of the electromagnetic shield being analyzed. In Step 104, electromagnetic waves corresponding to the converted signal are transmitted from a first antenna toward a second antenna without an electromagnetic shield being positioned between the two antennas. In Step 106, the electromagnetic waves received by the second antenna are converted to a corresponding signal that exhibits a third frequency, the third frequency being lower than the second frequency. In an exemplary embodiment, the third frequency may be a low frequency in a VHF radiofrequency range. In an exemplary embodiment, the frequency may be in a range from about 163 MHz to about 1 GHz. Other frequencies may be used in other embodiments depending upon the characteristics of the equipment and cabling being used. In Step 108, the amplitude of the corresponding signal exhibiting the third frequency is determined. The determined amplitude may be used as a reference amplitude.

Referring to FIG. 4B, Step 110 shows another phase of the method wherein an electromagnetic shield may be placed between the two antennas. The method illustrated in FIG. 4B is substantially the same as the method illustrated in FIG. 4A except that the two antennas are positioned on different sides of an electromagnetic shield. For example, the transmitting antenna may be inside an electromagnetically shielded shelter or enclosure and the receiving antenna may be outside the shelter or enclosure. In Step 110, the electromagnetic waves from the first antenna are transmitted toward the second antenna with the electromagnetic shield being positioned between the two antennas. In Step 112, attenuated remnants of the electromagnetic waves received by the second antenna may be converted to a second corresponding signal that exhibits a fourth frequency. The fourth frequency may be lower than the second frequency. In an exemplary embodiment, the fourth frequency may be a low frequency in a VHF radiofrequency range between about 163 MHz to about 1 GHz. Other frequencies may be used in other embodiments.

In Step 114, an amplitude of the corresponding signal may be determined. This amplitude is a second amplitude. In Step 116, the second amplitude may be compared to the reference amplitude.

Although the exemplary method first describes steps that are taken without an electromagnetic shield positioned between two antennas, the method may be performed in a way that Steps 110-114 described in FIG. 4B are followed before the steps described in FIG. 4A are followed and before there is a comparison of the two amplitudes.

In an alternative embodiment, a reference amplitude may be provided by another method. If the reference amplitude is provided by another method, the steps illustrated in FIG. 4A may not have to be followed. Instead, the method illustrated in FIG. 4B may be followed after the reference amplitude is determined. Alternatively, Steps 110-114 in the method illustrated in FIG. 4B may be followed before a reference amplitude is determined, after which Step 116 may be performed.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for determining the effectiveness of an electromagnetic shield to shield electromagnetic waves in a microwave frequency range by determining a level of amplitude attenuation of the electromagnetic waves impacting the electromagnetic shield, the system comprising:
   a signal generator for producing a first signal exhibiting a first frequency that is lower than the microwave frequency range;
   a first converter coupled to the signal generator for changing the first signal to a second signal exhibiting a second frequency that is within the microwave frequency range and is higher than the first frequency;
   a first antenna for converting the second signal to electromagnetic waves substantially exhibiting the second frequency and for transmitting the electromagnetic waves toward the electromagnetic shield;
   a second antenna for receiving remnants of the electromagnetic waves attenuated by the electromagnetic shield and for converting the remnants to a third signal substantially exhibiting the second frequency;
   a second converter for converting the third signal to a fourth signal exhibiting a third frequency lower than the second frequency; and
   a measuring receiver coupled to the second converter for determining amplitude of the fourth signal.

2. The system of claim 1, wherein the second antenna receives the attenuated remnants of the electromagnetic waves after the electromagnetic waves pass through the electromagnetic shield.

3. The system of claim 1, wherein the first antenna is positioned on a side of the electromagnetic shield and the second antenna is positioned on a second side of the electromagnetic shield.

4. The system of claim 1, wherein the first frequency is within a VHF range of frequencies.

5. The system of claim 1, wherein the third frequency is within a VHF range of frequencies.

6. The system of claim 1, wherein the first antenna is an omnidirectional antenna.

7. The system of claim 1, wherein the first antenna is a directional antenna.

8. The system of claim 1, wherein the first converter is operable to convert the first signal to a second frequency selected from a range of frequencies higher than the first frequency.

9. The system of claim 8, wherein the range of frequencies is from 10 GHz to 10.3 GHz.

10. The system of claim 1, wherein the electromagnetic shield is a shielded enclosure or a shielded shelter, the signal generator and the first antenna being adapted to be positioned inside the shielded enclosure or the shielded shelter.

11. The system of claim 10, wherein the second antenna is adapted to be positioned outside the shielded enclosure or the shielded shelter.

12. A system for determining the effectiveness of an electromagnetic shield to shield electromagnetic waves in a microwave frequency range by determining an attenuation level of the electromagnetic waves impacting the electromagnetic shield, the system comprising:
   a first converter receiving a first signal exhibiting a first frequency that is lower than the microwave frequency range and converting the first signal to a second signal exhibiting a second frequency that is within the microwave frequency range and is higher than the first frequency;
   a first antenna positioned on a side of the electromagnetic shield receiving the second signal for transmitting corresponding electromagnetic waves substantially exhibiting the second frequency through the electromagnetic shield toward a second antenna positioned on another side of the electromagnetic shield, the second antenna receiving attenuated remnants of the electromagnetic waves attenuated by the electromagnetic shield and producing a corresponding third signal substantially exhibiting the second frequency;

a second converter for converting the third signal to a fourth signal exhibiting a third frequency lower than the second frequency for transmission to a measuring receiver.

13. A system for determining an attenuation level of electromagnetic waves impacting an electromagnetic shield, the system comprising:

a first converter receiving a first signal exhibiting a first frequency and converting the first signal to a second signal exhibiting a second frequency higher than the first frequency;

a first antenna positioned on a side of the electromagnetic shield receiving the second signal for transmitting corresponding electromagnetic waves substantially exhibiting the second frequency through the electromagnetic shield toward a second antenna positioned on another side of the electromagnetic shield, the second antenna receiving attenuated remnants of the electromagnetic waves attenuated by the electromagnetic shield and producing a corresponding third signal substantially exhibiting the second frequency;

a second converter for converting the third signal to a fourth signal exhibiting a third frequency lower than the second frequency for transmission to a measuring receiver, and an attenuator coupled between the first converter and the first antenna for decreasing amplitude of the signal transmitted to the first antenna and to the measuring receiver for testing accuracy of the attenuation determination.

14. A method for determining an attenuation level of electromagnetic waves impacting an electromagnetic shield, the method comprising:

converting a produced signal exhibiting a first frequency to a converted signal exhibiting a second frequency higher than the first frequency;

transmitting electromagnetic waves corresponding to the converted signal from a first antenna toward a second antenna without the electromagnetic shield positioned between the first antenna and the second antenna;

converting the electromagnetic waves received by the second antenna to a corresponding signal exhibiting a third frequency lower than the second frequency;

determining a first amplitude of the corresponding signal, thereby providing a reference amplitude;

transmitting the electromagnetic waves corresponding to the converted signal from the first antenna toward the second antenna with the electromagnetic shield positioned between the first antenna and the second antenna;

converting attenuated remnants of the electromagnetic waves received by the second antenna to a second corresponding signal exhibiting a fourth frequency lower than the second frequency;

determining a second amplitude of the second corresponding signal; and comparing the second amplitude to the reference amplitude.

15. The method of claim 14, wherein the second frequency is a microwave.

16. The method of claim 14, wherein at least one of the third frequency and the fourth frequency is selected from a VHF range of frequencies.

17. The method of claim 14, wherein the fourth frequency is substantially the same frequency as the second frequency.

* * * * *